United States Patent [19]

Tabohashi et al.

[11] Patent Number: 4,880,561

[45] Date of Patent: Nov. 14, 1989

[54] OPTICALLY ACTIVE COMPOUND AND LIQUID CRYSTALLINE COMPOSITION

[75] Inventors: Tatsuru Tabohashi; Takao Sakurai; Ryoichi Higuchi; Naoko Mikami; Eri Yamamoto; Koji Takeuchi, all of Kawasaki, Japan

[73] Assignee: Ajinomoto Co., Inc., Tokyo, Japan

[21] Appl. No.: 38,897

[22] Filed: Apr. 16, 1987

[30] Foreign Application Priority Data

Apr. 21, 1986 [JP] Japan ............... 61-091859
Sep. 24, 1986 [JP] Japan ............... 61-225713

[51] Int. Cl.$^4$ ............ C09K 19/34; C09K 19/30; C07C 69/76; C07C 69/74
[52] U.S. Cl. ............ 252/299.61; 252/299.01; 252/299.63; 544/315; 544/318; 544/335; 544/298; 558/414; 558/416; 558/426; 560/59; 560/124
[58] Field of Search .......... 252/299.01, 299.61, 252/299.63; 350/350.5; 560/59, 124; 544/335, 298, 315, 318; 558/414, 416, 426

[56] References Cited

U.S. PATENT DOCUMENTS 4,638,073 1/1987 Walba et al. ............ 252/299.61

OTHER PUBLICATIONS

Petrzilka et al., Mol. Cryst. Liq. Cryst., Vol. 133, pp. 85–96 (1986).

*Primary Examiner*—John F. Terapane
*Assistant Examiner*—J. E. Thomas
*Attorney, Agent, or Firm*—Oblon, Spivak, McClelland, Maier & Neustadt

[57] ABSTRACT

Disclosed is an optically active cyclopropane compound represented by the formula (1):

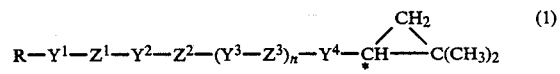

wherein R is an alkyl or cycloalkyl group, n is 0 or 1, $Y^4$ is —$CO_2CH_2$—, —OCO— or —$OCH_2$—, $Y^1$, $Y^2$ and $Y^3$ independently represent —$CO_2$—, —OCO—, —O—, a direct bond or —$CH_2O$—, $Z^1$, $Z^2$, and $Z^3$ independently represent

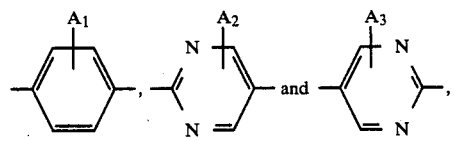

$A^1$, $A^2$ and $A^3$ independently represent fluorine, bromine, chlorine, a cyano group or hydrogen, and the mark $\underset{*}{C}$ indicates an asymmetric carbon atom. The optically active cyclopropane compound includes a compound which exhibits a ferroelectric liquid crystalline characteristic, and a compound which does not exhibit a ferroelectric liquid characteristic when used alone, but, can be used as a constituent of a ferroelectric liquid crystal composition.

9 Claims, 2 Drawing Sheets

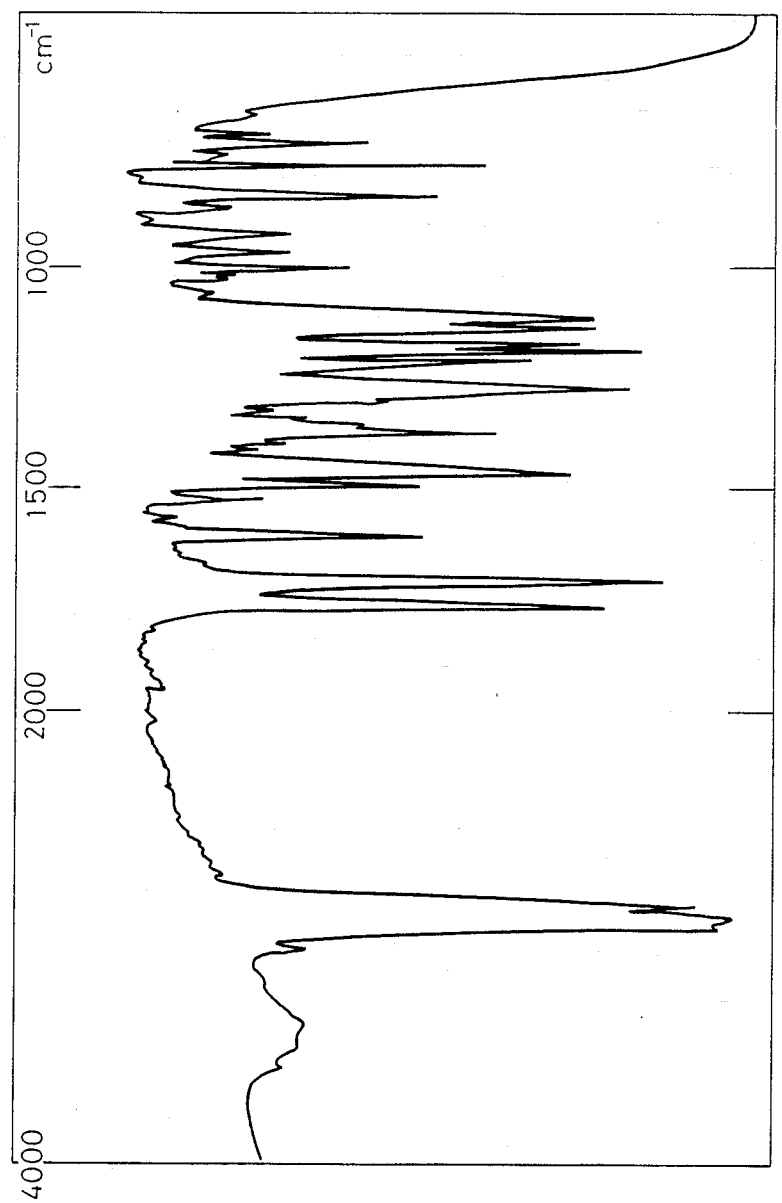

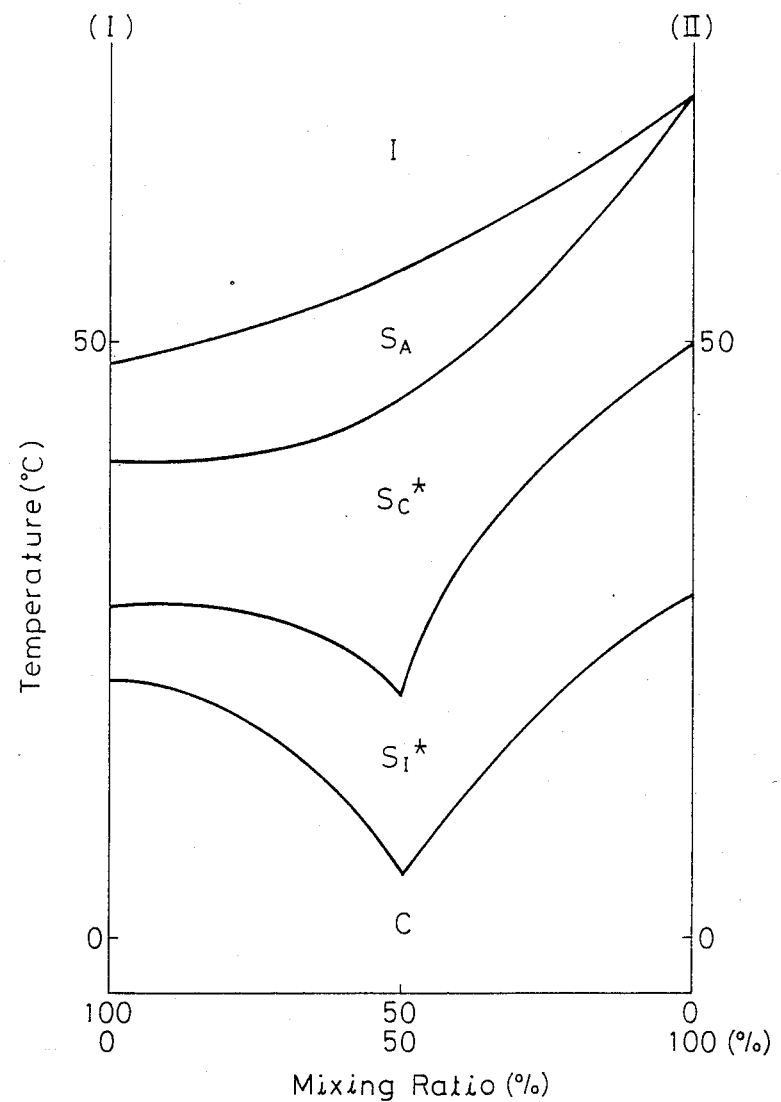

OPTICALLY ACTIVE COMPOUND AND LIQUID CRYSTALLINE COMPOSITION

BACKGROUND OF THE INVENTION

(1) Field of the Invention

The present invention relates to a novel, optically active cyclopropane compound and a liquid crystal composition comprising this optically active cyclopropane compound.

This optically active cyclopropane compound is valuable as an optical switch element material, especially a material of a ferroelectric liquid crystal composition.

In the instant specification, by the term "liquid crystalline substance or material" is meant not only a substance showing a liquid crystalline phase but also a substance or material which is valuable as a constituent of a liquid crystal composition though it is not detected that the substance or material shows a liquid crystalline phase.

(2) Description of the Related Art

As the display system using a liquid crystal display element, which is widely utilized in practice at present, there can be mentioned the twisted nematic type (TN type) and the dynamic scattering type (DS type). In these display systems, display is performed by a nematic liquid crystalline cell comprising a nematic liquid cell as the main component. One defect of the conventional nematic liquid cell is a low response speed, and only a response speed of several milliseconds is obtained. This defect is one cause of the limitation of the application range of the nematic liquid cell. Recently, however, it has been found that a high response speed can be obtained if a smectic liquid crystalline cell is used.

It has been clarified that some optically active smectic liquid crystals have a ferroelectric property, and there are great expectations on the utilization of such liquid crystals. Liquid crystals having a ferroelectric property, that is, ferroelectric liquid crystals, are compounds synthesized by R. B. Meyer et al in 1975, which are represented by 2-methylbutyl 4-(4-n-decyloxybenzilydeneamino)cinnamate (hereinafter referred to as "DOBAMBC"). The compounds are characterized as exhibiting a ferroelectric property in the chiral smectic C phase (hereinafter referred to as "SmC* phase") [J. Physique, 36, L-69 (1975)].

N. A. Clark et al found that a high-response speed of an order of microseconds is obtained in a film cell of DOBAMBC [Appl. Phys. Lett., 36, 89 (1980)], and with this finding as a momentum, the ferroelectric crystal has attracted attention as a material applicable not only to a display system such as a liquid crystal television but also to an optical printer head, an optical Fourier converting element, a light valve, and other optoelectronic elements because of high-speed response characteristics.

Since DOBAMBC has a small spontaneous polarization and is a Schiff base, it has poor physical and chemical stabilities. Accordingly, various physically and chemically stable compounds have been investigated as ferroelectric liquid crystalline materials. At present, research work on the development of ferroelectric liquid crystalline materials is concentrated on an enhancement of the high-speed response characteristic, orientation effect, contrast characteristic, memory characteristic, and threshold value characteristic, and optimization of practical properties such as the temperature dependencies of these characteristics.

However, none of the known ferroelectric liquid crystals, when used alone, shows a large spontaneous polarization, a low viscosity, a long helical pitch and an appropriate molecular tilt angle within a broad temperature range including room temperature such that the above-mentioned practically desired properties are manifested. Therefore, practically, attempts have been made to optimize the foregoing characteristics by mixing several compounds such as a compound having or inducing a large spontaneous polarization, a compound having a low viscosity and compounds having reverse helical pitches. The incorporation of a ferroelectric liquid crystal showing a ferroelectric characteristic within a broad temperature range or a smectic C liquid crystal which is not chiral is effective for obtaining a liquid crystal composition showing a ferroelectric characteristic within a broad temperature range. In connection with liquid crystalline materials used for ferroelectric liquid crystal compositions, it is considered necessary to optimize the physical properties by selecting (1) a compound having or inducing a large spontaneous polarization, (2) a compound considered from the skeleton to have a low viscosity or a compound not degrading the liquid crystalline property of a compound considered from the skeleton to have a low viscosity when both are mixed, (3) a compound having a short helical pitch and capable of unwinding the helical pitch by the addition thereof in a minor amount, and (4) a liquid crystalline substance showing a ferroelectric property within a broad temperature range, among a great number of compounds differing in the skeleton and optically active group, and mixing them together.

The presence of an optically active group is indispensable for a compound to be a ferroelectric liquid crystal. Amyl alcohol, octyl alcohol and the like are mentioned as the known optical activity source. Although these alcohols are easily available, they are monohydric alcohols having poor reactivity, and chemical modification in the vicinity of the optically active site is limited and the molecular design of a liquid crystalline substance is therefore difficult. As a typical instance of this chemical modification, there can be mentioned only the carbon number-increasing reaction proposed by A. Hallsby et al [Mol. Cryst. Liq. Cryst., 1982 (62), L61] or J. W. Goodby et al [Mol. Cryst. Liq. Cryst., 1984 (110), 175–203].

As the effect of the optically active group or the neighbouring substituent, there can be mentioned the steric factor and electronic factor of the asymmetric source. As the effect on the physical properties of the liquid crystalline material, the former factor has an influence on the symmetry of the liquid crystalline molecule and, for example, control of the range of temperatures showing the liquid crystalline phase becomes possible. The latter factor gives a change to the optically active group or the neighbouring dipole moment and control of the direction and magnitude of the spontaneous polarization, the length and direction of the pitch and the viscosity becomes possible Accordingly, if the effects of the optically active group or the neighbouring substituent are effectively controlled, the molecular design of a compound satisfying the requirements of various characteristics such as temperature range, response speed, viscosity and pitch length, which are imposed on a ferroelectric liquid crystalline material ensuring realization of large-scale liquid crystal panel display, or the design of a composition of such compounds will be easily accomplished.

SUMMARY OF THE INVENTION

We investigated liquid crystalline substances obtained from various asymmetric sources and found optically active cyclopropane compounds having a performance equal or superior to those of liquid crystalline substances obtained from non-cyclic alcohols such as amyl alcohol and octyl alcohol. We have now completed the present invention based on this finding.

It is a primary object of the present invention to provide novel optically active cyclopropane compounds which either exhibit a ferroelectric liquid crystalline characteristic or do not exhibit a ferroelectric liquid crystalline characteristic but can be effectively used as a constituent of a ferroelectric liquid crystal composition, which have a relatively large spontaneous polarization, and which exhibit a high-speed response In one aspect of the present invention, there is provided an optically active cyclopropane liquid crystalline compound represented by the following formula (1):

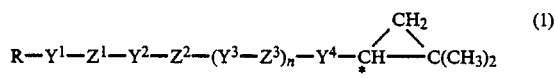

wherein R represents a linear or branched alkyl group having 4 to 18 carbon atoms or a cycloalkyl group having 4 to 18 carbon atoms, n is 0 or 1, $Y^4$ represents $-CO_2CH_2-$, $-OCO-$ or $-OCH_2-$, $Y^1$, $Y^2$ and $Y^3$ independently represent $-CO_2-$, $-OCO-$, $-O-$, a direct bond or $-CH_2O-$, $Z^1$, $Z^2$, and $Z^3$ are independently selected from

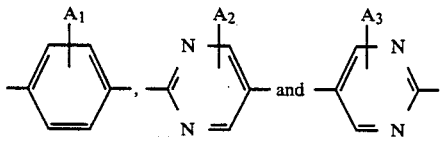

and at least two of the groups optionally selected as $Z^1$, $Z^2$ and $Z^3$ may be the same or different, $A^1$, $A^2$ and $A^3$ independently represent a fluorine atom, a bromine atom, a chlorine atom, a cyano group or a hydrogen atom, and the mark $$\underset{*}{C}$$

indicates an asymmetric carbon atom.

In another aspect of the present invention, there is provided a liquid crystal composition comprising at least one optically active cyclopropane compound represented by the above formula (1).

BRIEF DESCRIPTION OF THE DRAWINGS

FIG. 1 shows the IR spectrum of the optically active cyclopropane compound obtained in Example 1, and FIG. 2 is a phase diagram of a composition comprising 4'-octylcarbonyloxy-4-(1S-2,2-dimethylcyclopropanemethyloxycarbonyl)biphenyl and 4'-heptylcarbonyloxy-4-(1S-chloro-2-methylbutylcarbonyloxy)-biphenyl.

DESCRIPTION OF THE PREFERRED EMBODIMENTS

In general, liquid crystalline compounds have a rod-like structure comprising a nuclear portion composed of a benzene ring or the like and a linear portion composed of an alkyl chain or the like. It is known that compounds in which the carbon number of the alkyl chain exceeds a certain level is apt to have the smectic phase. It also is known that compounds having the same skeleton show similar phase systems even if the carbon number of the alkyl chain differs to some extent. Compounds of the formula (1) in which R is an alkyl group having 6 to 14 carbon atoms are apt to show a chiral smectic C phase singly or in the form of a mixture, and they are especially valuable as ferroelectric liquid crystalline materials. Other compounds of the formula (1) can be used as additives to ferroelectric liquid crystals or as ordinary liquid crystalline materials.

The optically active cyclopropane compound of the present invention is valuable as a liquid crystalline substance, especially a ferroelectric liquid crystalline substance. The cyclopropane compound has a larger spontaneous polarization than other linear optically active alcohols Although a compound of the following formula (A):

shows a chiral smectic C phase ("SmC* phase") in the case of n=7 to 11 and a compound of the following formula (B):

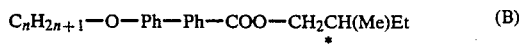

shows a SmC* phase in the case of n=7 to 12, the spontaneous polarization is up to 5 nC/cm² even at highest.

In contrast, the compound of the following formula (C) having a cyclopropane ring according to the present invention has a spontaneous polarization of 11 nC/cm², which is more than 2 times that of the compound (A) or (B):

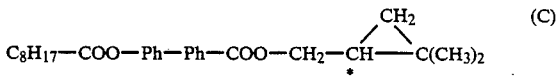

The reason why the cyclopropane compound of the present invention has a larger spontaneous polarization than the non-cyclic optically active alcohol such as amyl alcohol is considered to be that since the asymmetric source is present on the three-membered ring, the rotation freedom of the asymmetric source or neighbouring substituent is reduced and the steric conformation is fixed.

As is illustrated in the example given hereinafter, according to the present invention, there can be provided (1) compounds which do not degrade the liquid crystal characteristic of a compound considered from the skeleton to have a low viscosity when incorporated into this liquid crystalline compound and (2) compounds which have a short helical pitch and provide good compositions in which the helical pitch is unwound by incorporation of small amounts of said compounds.

As the compounds suitable for forming a ferroelectric liquid crystalline composition by mixing them with the optically active cyclopropane compound of the present invention, there can be mentioned compounds of the following groups (1), (2) and (3).

(1) Ferroelectric liquid crystals developed by us in the past, which are disclosed in Japanese Unexamined Patent Publication Nos. 60-67,453, 60-67,586, 60-168,780, 60-168,781 and 60-218,358, and Japanese Patent Application Nos. 59-189,232, 60-22,920, 60-87,034, 60-117,053, 60-144,136, 60-162,654, 60-162,656, 60-250,335, 60-272,834, and No. 60-291,179.

(2) Compounds having a smectic C phase, such as alkyl alkoxybiphenylcarboxylate, alkyl alkylcarbonyloxybiphenylcarboxylate, alkoxyphenyl alkoxybenzoate, alkyloxycarbonylphenyl alkoxybenzoate, alkoxyalkoxyphenyl alkoxybenzoate, alkoxybiphenyl alkoxybenzoate, alkoxyphenyl alkoxybiphenylcarboxylate, alkoxybiphenyl alkylbenzoate, alkoxyphenyl alkylbiphenylcarboxylate, alkylbiphenyl alkoxybenzoate, alkylphenyl alkoxybiphenylcarboxylate, alkoxybiphenyl alkylcarbonyloxybenzoate, alkoxyphenyl alkylcarbonyloxybiphenylcarboxylate, alkylcarbonyloxybiphenyl alkoxybenzoate, alkylcarbonyloxyphenyl alkoxybiphenylcarboxylate, 5-alkyl-2-(4'-alkoxyphenyl)pyrimidine, 5-alkoxy-2-(4'-alkoxyphenyl)pyrimidine, 5-alkyl-2-(4'-alkylcarbonyloxyphenyl)pyrimidine, 5-alkoxy-2-(4'-alkylcarbonyloxyphenyl)pyrimidine, 5-alkyl-2-(4'-alkyloxycarbonylphenyl)pyrimidine, 5-alkoxy-2-(4'-alkyloxycarbonylphenyl)pyrimidine, 5-alkyl-2-(4'-alkoxyphenyl)pyrazine, 5-alkoxy-2-(4'-alkoxyphenyl)pyrazine, 5-alkyl-2-(4'-alkylcarbonyloxyphenyl)pyrazine, 5-alkoxy-2-(4'-alkylcarbonyloxyphenyl)pyrazine, 5-alkyl-2-(4'-alkyloxycarbonylphenyl)pyrazine, 5-alkoxy-2-(4'-alkyloxycarbonylphenyl)pyrazine, 3-(4'-alkylphenyl)-6-alkoxypyridazine, 3-(4'-alkoxyphenyl)-6-alkoxypyridazine, 3-(4'-alkoxyphenyl)-6-alkylpyridazine, 5-(4'-alkylphenyl)-2-(4''-alkoxyphenyl)pyrimidine, 5-(4'-alkoxyphenyl)-2-(4''-alkoxyphenyl)pyrimidine, 5-(4'-alkylphenyl)-2-(4''-alkylcarbonyloxyphenyl)pyrimidine, 5-(4'-alkoxyphenyl)-2-(4''-alkylcarbonyloxyphenyl)pyrimidine, 5-(4'-alkylphenyl)-2-(4''-alkyloxycarbonylphenyl)pyrimidine, 5-(4'-alkoxyphenyl)-2-(4''-alkyloxycarbonylphenyl)pyrimidine, 5-(4'-alkoxyphenyl)-2-(4''-alkoxyphenylcarbonyloxy)pyrimidine, 5-(4'-alkylphenyl)-2-(4''-alkoxyphenylcarbonyloxy)pyrimidine, 5-(4'-alkoxyphenyl)-2-(4''-alkylphenylcarbonyloxy)pyrimidine, alkylphenylcarbonyloxy)pyrimidine, 5-(4'-alkylphenyl)-2-(4''-alkoxyphenyl)-1,2,4-triazine, 5-(4'-alkoxyphenyl)-2-(4''-alkoxyphenyl)-1,2,4-triazine, 5-(4'-alkylphenyl)-2-(4''-alkylcarbonyloxyphenyl)-1,2,4-triazine, 5-(4'-alkoxyphenyl)-2-(4''-alkylcarbonyloxyphenyl)-1,2,4triazine, 5-(4'-alkylphenyl)-2-(4''-alkyloxycarbonylphenyl)-1,2,4-triazine and 5-(4'-alkoxyphenyl)-2-(4''-alkyloxycarbonylphenyl)-1,2,4-triazine.

(3) Ferroelectric liquid crystalline compounds showing a chiral smectic C phase, which are obtained by introducing an asymmetric carbon atom in the alkyl group, alkoxy group, alkylcarbonyloxy group or alkyloxycarbonyl group in the above-mentioned compounds of the group (2).

The cyclopropane compound of the formula (1) is derived, for example, from (+)-1S-2,2-dimethylcyclopropane-carboxylic acid of the following formula (D) as the asymmetric source:

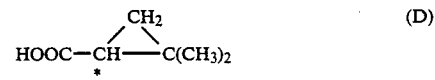

The compound of the formula (D) is synthesized according to a known process as disclosed in Japanese Unexamined Patent Publication No. 59-225,194. More specifically, isobutylene gas is reacted with ethyl diazoacetate in the presence of a catalytic amount of a copper complex of (R)-N-salicylydene-2-amino-1,1-di(2-butoxy-5-t-butylphenyl)-3-phenyl-1-propanol and a catalytic amount of phenylhydrazine and the reaction product is hydrolyzed to obtain the compound of the formula (D). The so-obtained (+)-1S-2,2-dimethylcyclopropane-carboxylic acid (D) or its active derivative is reacted with a phenol derivative, or the compound (D) is reduced to (+)-2,2-dimethyl-1S-hydroxymethylcyclopropane according to a known process and this compound is reacted with a benzoic acid derivative, whereby the optically active cyclopropane compound represented by the formula (1) is obtained.

The optically active cyclopropane compound of the present invention has a ferroelectric liquid crystalline characteristic. For example, 4'-octyloxy-4-(1S-2,2-dimethylcyclopropane-methyloxycarbonyl)biphenyl shows the SmC* phase at a temperature of from 27° to 40° C. and has a spontaneous polarization of 11 nC/cm$^2$.

The spontaneous polarization of the optically active compound of the present invention is relatively large, as pointed out above.

Although a certain optically active cyclopropane compound included within the scope of the present invention is not a ferroelectric liquid crystal when used alone, this compound can be effectively used as a constituent of a ferroelectric liquid crystal composition. As shown in the examples given hereinafter, some of optically active cyclopropane compounds of the present invention are substances showing no liquid crystalline phase when used alone, but there are included compounds having a short inherent helical pitch such as 0.1 μm and if small amounts of such compounds are incorporated into ferroelectric liquid crystalline compounds or compositions having a reverse helical pitch, there can be obtained ferroelectric liquid crystal compositions having a long helical pitch.

For example, as illustrated in the examples given hereinafter, if S-type optically active cyclopropane compounds of the present invention, which have a counterclockwise helical pitch, are mixed with natural amino acid derivatives, that is, ferroelectric liquid crystals having a clockwise helical pitch and a very large spontaneous polarization, which were developed by us in the past and are disclosed in Japanese Unexamined Patent Publication No. 60-218,358 and Japanese Patent Application Nos. 59-189,232, 60-22,920, 60-87,034, 60-117,053, 60-144,136, 60-162,654, 60-291,179, ferroelectric liquid crystal compositions having an elongated helical pitch providing a good orientation can be obtained.

The optically active cyclopropane compound of the present invention or an optical active liquid crystal composition comprising the optically active cyclopropane compound of the present invention can be added to a nematic liquid crystal for color display of the White-Taylor type, display of the cholesteric-nematic phase transition type and prevention of generation of the reverse domain in a TN-type cell.

Since a liquid crystal composition comprising the cyclopropane compound of the present invention is a smectic liquid crystal, the liquid composition can be used for a memory type display element of the heat writing type or laser writing type.

The present invention will now be described in detail with reference to the following examples that by no means limit the scope of the invention.

In the examples, C, SX, S*, Sc*, Sa, N*, N and I phases represent a crystal phase, a smectic phase not clearly identified, a chiral smectic phase not clearly identified, a chiral smectic C phase, a smectic A phase, a chiral nematic phase, a nematic phase and an isotropic phase, respectively.

The compounds of the present invention were purified by silica gel chromatography and recrystallization from an alcohol or hexane. The measured values of the phase transition points, shown hereinafter, will be influenced by the purities of substances.

EXAMPLE 1

Synthesis of 4'-octylcarbonyloxy-4-(1S-2,2-dimethylcyclopropane-methyloxycarbonyl)biphenyl (a) A 100-ml three-neck flask equipped with a constant pressure dropping funnel, a magnetic stirrer and a reflux condenser was charged with 30 ml of anhydrous ether and 0.8 g (21.1 millimoles) of lithium aluminum hydride after sufficient substitution of the inner atmosphere with nitrogen The reactor was cooled to 0° C. and 2.1 g (16.3 millimoles) of ethyl (+)-1S-2,2-dimethylcyclopropane-carboxylate obtained according to the known process and 20 ml of anhydrous ether were carefully dropped with stirring over a period of about 15 minutes. After completion of the dropwise addition, the temperature was returned to room temperature and the mixture was stirred for about 1 hour. Then, 20 ml of water was added to the reaction mixture to effect hydrolysis, and an excess of sodium chloride was added and ether extraction carried out. The ether layer was washed with a saturated aqueous solution of sodium chloride and dried on anhydrous magnesium sulfate. Ether was removed by distillation and the residue subjected to distillation under reduced pressure to obtain 1.27 g (12.6 millimoles) of (+)-2,2-dimethyl-1S-hydroxymethylcyclopropane as a fraction boiling at 62 to 63° C under 70 mmHg.

(b) A 100-ml flask was charged with 0.58 g (5.79 millimoles) of (+)-2,2-dimethyl-1S-hydroxymethylcyclopropane, 20 ml of carbon tetrachloride and 5 ml of pyridine, and then 2.0 g (5.91 millimoles) of an acid chloride derivative from 4'-octylcarbonyloxybiphenyl-4-carboxylic acid and 20 ml of carbon tetrachloride were dropped. The mixture was allowed to stand overnight and the reaction liquid was poured into ice water, followed by neutralization with dilute hydrochloric acid, extraction with chloroform, washing, drying and removal of the solvent by distillation. The residue was purified by silica gel column chromatography (developing solvent=chloroform/carbon tetrachloride mixed solvent of 2/5) and recrystallized from ethanol to obtain 0.8 g of 4'-octylcarbonyloxy-4-(1S-2,2-dimethylcyclopropanemethyloxycarbonyl)biphenyl, the infrared (IR) spectrum of which is shown in FIG. 1.

When the obtained compound was sealed in a cell and the transition temperatures were measured, the following results were obtained.

At elevation of temperature:
C-30-Sc*-40-Sa-48-I

At lowering of temperature:
C-9-SX-21-S*-27-Sc*-40-Sa-48

The spontaneous polarization of the above compound was 11 nC/cm$^2$ as determined according to the Sawyer-Tower method.

EXAMPLE 2

When 4'-octylcarbonyloxy-4-(1S-2,2-dimethylcyclopropane-methyloxycarbonyl)biphenyl obtained in Example 1 was mixed with 4'-heptylcarbonyloxy-4-(1S-chloro-2-methylbutylcarbonyloxy)biphenyl at a weight ratio of 1/1, a composition showing the SmC* phase at a temperature of from 5 to 25° C. was obtained. The phase diagram of the composition is shown in FIG. 2.

EXAMPLE 3

Synthesis of 4'-octyloxy-4-(1S-2,2-dimethylcyclopropane-carbonyloxy)biphenyl

An acid chloride derived from (+)-1S-2,2-dimethyl-cyclopropane-carboxylic acid was reacted with p-(p'-octyloxyphenyl)-phenol in pyridine as the solvent. The reaction mixture was allowed to stand overnight and poured into ice water, followed by neutralization with dilute hydrochloric acid, extraction with chloroform, washing, drying and removal of the solvent by distillation. The residue was purified by silica gel column chromatography (developing solvent =chloroform/carbon tetrachloride mixed solvent of 1/3) and recrystallized from methanol to obtain 4'-octyloxy-4-(1S-2,2-dimethylcyclopropane-carbonyloxy)biphenyl having a melting point of 72° C.

EXAMPLES 4 through 6

The following compounds were synthesized in the same manner as described in Example 3 except that p-(p'-alkyloxyphenyl)-phenols were used instead of p-(p'-octyloxyphenyl)-phenol.

4'-Butyloxy-4-(1S-2,2-dimethylcyclopropanecarbonyloxy)biphenyl having a melting point of 90° C.

4'-Dodecyloxy-4-(1S-2,2-dimethylcyclopropanecarbonyloxy)biphenyl having a melting point of 70° C.

4'-Hexadecyloxy-4-(1S-2,2-dimethylcyclopropanecarbonyloxy)biphenyl having a melting point of 79° C.

EXAMPLE 7

4'-Octylcarbonyloxy-4-(1S-2,2-dimethylcyclopropanecarbonyloxy)biphenyl was synthesized in the same manner as described in Example 3 except that p-(p'-octylcarbonyloxyphenyl)-phenol was used instead of p-(p'-octyloxyphenyl)-phenol. The melting point of the obtained compound was 72° C.

EXAMPLE 8

4'-Nonyloxycarbonyloxy-4-(1S-2,2-dimethylcyclopropane-carbonyloxy)biphenyl was synthesized in the same manner as described in Example 3 except that p-(p'-nonyloxycarbonyloxyphenyl)-phenol was used instead of p-(p'-octyloxyphenyl)-phenol. The melting point of the obtained compound was 57° C.

EXAMPLE 9

2-[4-(1S-2,2-Dimethylcyclopropane-carbonyloxy)-phenyl]-5-dodecylpyrimidine was synthesized in the same manner as described in Example 3 except that 2-(4-hydroxyphenyl)-5-dodecylpyrimidine was used instead of p-(p'-octyloxyphenyl)-phenol. The melting point of the obtained compound was 70° C.

EXAMPLES 10 through 12

The following compounds were synthesized in the same manner as described in Example 3 except that 2-(4-alkoxyphenyl)-5-hydroxypyrimidines were used instead of p-(p'-octyloxyphenyl)-phenol.

2-(4-Heptyloxyphenyl)-5-(1S-2,2-dimethylcyclopropane-carbonyloxy)pyrimidine having a melting point of 96° C. propane-carbonyloxy)pyrimidine having a melting point of 97° C.

2-(4-Dodecyloxyphenyl)-5-(1S-2,2-dimethyl- cyclopropane-carbonyloxy)pyrimidine having a melting point of 102° C.

EXAMPLE 13

Bis-[p-(1S-2,2-dimethylcyclopropane-carbonyloxy)-phenyl] was synthesized in the same manner as described in Example 3 except that p,p'-biphenol was used instead of p-(p'-octyloxyphenyl)-phenol. The melting point of the obtained compound was 138° C.

EXAMPLE 14

By mixing compounds of the present invention with compounds having the smectic C phase, there was prepared a composition comprising 4.6% by weight of 4'-butyloxy-4-(1S-2,2-dimethylcyclopropane-carbonyloxy)biphenyl, 4.6% by weight of 4'-octyloxy-4-(1S-2,2-dimethyl- cyclopropane-carbonyloxy)biphenyl, 4.6% by weight of 4'-dodecyloxy-4-(1S-2,2-dimethylcyclopropanecarbonyloxy)biphenyl, 4.6% by weight of 4'-hexadecyloxy-4(1S-2,2-dimethylcyclopropane-carbonyloxy)biphenyl, 4.6% by weight of 4'-nonyloxycarbonyloxy-4-(1S-2,2-dimethylcyclopropane-carbonyloxy)biphenyl, 4.6% by weight of 2-[4-(1S-2,2-dimethylcyclopropane-carbonyloxy)phenyl]-5-dodecylpyrimidine, 43.4% by weight of 2-(4'-nonyloxy)phenyl-5-nonylpyrimidine and 30.0% by weight of 4-nonyloxyphenyl 4-octyloxybenzoate.

The composition showed the ferroelectric liquid crystalline phase even to a temperature below 0° C. and had the following phase transition points Sc*-Sa phase transition point: 51° C.
Sa-N* phase transition point: 52° C.
N*-I phase transition point: 62° C.

As apparent from the foregoing description, even an optically active cyclopropane compound included within the scope of the present invention, which is not a ferroelectric liquid crystal when used alone, is effectively used for forming a liquid crystal composition showing ferroelectric characteristics at room temperature by mixing this compound with a compound having the smectic C phase.

EXAMPLE 15

Compounds of the present invention were mixed with a ferroelectric liquid crystal composition having a clockwise helical pitch to obtain a composition having an unwound helical pitch and comprising 4.0% by weight of 4'-butyloxy-4-(1S-2,2-dimethylcyclopropanecarbonyloxy)biphenyl, 4.0% by weight of 4'-octyloxy-4-(1S-2,2-dimethylcyclopropane-carbonyloxy)biphenyl, 4.0% by weight of 4'-dodecyloxy-4-(1S-2,2-dimethyl- cyclopropane-carbonyloxy)biphenyl, 4.0% by weight of 4'-hexadecyloxy-4-(1S-2,2-dimethylcyclopropane-carbonyloxy)biphenyl, 4.0% by weight of 4'-nonyloxycarbonyloxy-4-(1S-2,2-dimethylcyclopropane-carbonyloxy)biphenyl, 4.0% by weight of 2-[4-(1S-2,2-dimethylcyclopropane-carbonyloxy)phenyl)-5-dodecylpyrimidine, 12.4% by weight of (1S,2S)-4''-(4'-octyloxyphenyl)phenyl 1-chloro-2-methylpentanoate, 12.4% by weight of (1S,2S)-4''-(4'-nonylcarbonyloxyphenyl)phenyl 1-chloro-2-methylpentanoate, 12.4% by weight of (1S)-4''-(4'-nonylcarbonyloxyphenyl)phenyl 1-chloro-2-methylbutanoate and 38.8% by weight of (1S,2S)-4''-[4'-(1-chloro-2-methylpentylcarbonyloxy)-phenyl]phenyl 4'''-octylcarbonyloxy-3'''-chlorobenzoate. In this composition, the helical pitch of the chiral nematic phase was infinitely diffused, and the orientation was very good.

The composition showed the ferroelectric liquid crystalline phase even to a temperature below 0° C. and had the following phase transition points.

Sc*-Sa phase transition point: 63° C.
Sa-N* phase transition point: 65° C.
N*-I phase transition point: 70° C.

The composition was sealed in a cell formed by spin-coating a polyimide on Nesa glass and rubbing the coating and having a spacer of a polyethylene terephthalate film having a thickness of 2.5 μm, and the composition was gradually cooled from the isotropic phase at a rate of 0.1° C. per minute, whereby a cell having a good orientation was obtained. A rectangular wave of 40 Vp-p was applied to the cell and the electrooptic effect was observed by a polarization microscope. A high-speed response was obtained at a very clear contrast. Thus, it was confirmed that this composition could be applied to liquid crystal display.

As apparent from the foregoing illustration, even optically active compounds of the present invention which are not ferroelectric liquid crystals when used alone are very valuable for forming liquid crystal compositions having a high-response speed and a very good orientation of an unwound helical pitch and showing ferroelectric characteristics at room temperature by mixing these compounds with other ferroelectric liquid crystalline compounds having a reverse helical pitch

EXAMPLE 16

4'-Octyloxy-4-(1S-2,2-dimethylcyclopropane-carbonyloxy)phenyl obtained in Example 3 is not a ferroelectric liquid crystalline compound when used alone, but since the inherent helical pitch of this compound is counterclockwise and is as short as 0.1 μm, the compound is very effective for unwinding an inherent clockwise helical pitch of a ferroelectric liquid crystal composition by addition of a small amount of said compound.

The above-mentioned compound obtained in Example 3 was mixed with a clockwise ferroelectric liquid crystal composition and further with Sc phase compounds, which were not chiral, to obtain a composition having an unwound helical pitch and comprising 7.7% by weight of 4'-octyloxy-4-(1S-2,2-dimethylcyclopropane-carbonyloxy)biphenyl, 8.85% by weight of (1S,2S)-4''-(4'-octyloxyphenyl)phenyl 1-chloro-2-methylpentanoate, 3.75% by weight of (1S,2S)-4''-(4'-nonyloxycarbonyloxyphenyl)phenyl 1-chloro-2-methyl-pentanoate, 4.25% by weight of (1S,2S)-4''-(4'-nonylcarbonyloxyphenyl)phenyl 1-chloro-2-methylpentanoate, 4.25% by weight of (1S)-4''-(4'-nonylcarbonyloxyphenyl) 1-chloro-2-methylbutanoate, 7.3% by weight of (1S,2S)-4''-[4'-(1-chloro-2-methylpentylcarbonyloxy)phenyl]-phenyl 4'''-octylcarbonyloxy-3'''chlorobenzoate, 13.15% by weight of (S)-4'-(2''-methylbutyloxy)-phenyl-4-octyloxybenzoic acid, 16.45% by weight of 2-(4'-octyloxy)phenyl-5-octylpyrimidine, 16.45% by weight of 2-(4'-nonyloxy)phenyl-5octylpyrimidine and 16.45% by weight of 2-(4'-decyloxy)phenyl-5-octylpyrimidine. In this composition, the helical pitch of the chiral nematic phase was indefinitely diffused, and the composition had a very good orientation.

The composition showed the ferroelectric liquid crystalline phase even to a temperature lower than the ice point, and the composition had the following phase transition points.

Sc*-Sa phase transition point: 54° C.
Sa-N* phase transition point: 56° C.
N*-I phase transition point: 60° C.

The composition was sealed in a cell formed by spin-coating a polyimide on Nesa glass and rubbing the coating and having a spacer of a polyethylene terephthalate film having a thickness of 2.5 μm, and the composition was gradually cooled from the isotropic phase at a rate of 0.1° C. per minute, whereby a cell having a good orientation was easily obtained A rectangular wave of 40 Vp-p was applied to the cell and the electro-optic effect was observed by a polarization microscope. A very clear contrast was seen. It was proved that the composition could be applied to a liquid crystal display. When the response speed of this cell was measured by using a photosemiconductor, it was found that the response speed required for changing the quantity of transmitted light from 10% to 90% was about 10 microseconds at room temperature, and thus it was confirmed that the response speed was very high.

As apparent from the foregoing illustration, even an optically active cyclopropane compound of the present invention, which is not a ferroelectric liquid crystal when used alone, is valuable for obtaining a liquid crystal composition having a high-speed response characteristic and a very good orientation of an unwound helical pitch and showing a ferroelectric characteristic at room temperature by mixing said compound with a ferroelectric liquid crystalline compound having a reverse helical pitch or a compound showing the smectic C phase.

EXAMPLE 17

2-(4-Decyloxyphenyl)-5-(1S-2,2-dimethylcyclopropane-carbonyloxy)pyrimidine obtained in Example 11 is not a ferroelectric liquid crystalline compound when used alone, but since the inherent helical pitch is counterclockwise and as short as 0.1 μm, the compound is valuable for unwinding the inherent helical pitch of a clockwise ferroelectric liquid crystal composition by addition of a small amount of this compound This compound obtained in Example 11 was mixed with a clockwise ferroelectric liquid crystal composition and further with an Sc compound which was not chiral, to obtain a composition having an unwound helical pitch and comprising 10.8% by weight of 2-(4-decyloxyphenyl)-5-(1S-2,2-dimethylcyclopropane-carbonyloxy)pyrimidine, 39.2% by weight of (1S,2S)-4''-(4'-octyloxyphenyl)phenyl 1-chloro-2-methylpentanoate, 30.0% by weight of 2-(4'-nonyloxy)phenyl-5-nonylpyrimidine and 20.0% by weight of 4-nonyloxyphenyl 4-octyloxybenzoate. The composition showed the ferroelectric liquid crystalline phase even to a temperature below 0° C. and had the following phase transition points.

Sc*-Sa phase transition point: 47° C.
Sa-N* phase transition point: 53° C.
N*-I phase transition point: 58° C.

The composition was sealed in a cell formed by spin-coating a polyimide on Nesa glass and rubbing the coating and having a spacer of a polyethylene terephthalate film having a thickness of 3.4 μm, and the composition was gradually cooled from the isotropic phase at a rate of 0.1° C. per minute, whereby a cell having a good orientation was easily obtained A rectangular wave of 58 Vp-p was applied to the cell and the electro-optical effect was observed by a polarization microscope. A very clear contrast was seen. Thus, it was proved that the composition could be applied to a liquid crystal display. When the response speed of the cell was measured by using a photosemiconductor, it was found that the response speed required for changing the quantity of transmitted light from 10% to 90% was about 30 microseconds at room temperature, and thus it was confirmed that the response speed was very high.

As apparent from the foregoing illustration, even an optically active cyclopropane compound of the present invention which is not a ferroelectric liquid crystal when used alone is valuable for forming a liquid crystal composition having a ferroelectric characteristic at room temperature, a high response speed and a very good orientation of an unwound helical pitch by mixing this compound with a ferroelectric liquid crystalline compound having a reverse helical pitch or a compound showing the smectic C phase.

We claim:

1. An optically active cyclopropane compound having the formula (I):

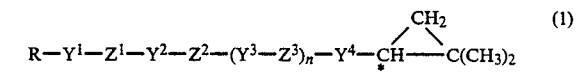

wherein R represents a linear or branched alkyl group of 4–18 carbon atoms or a cyclopropyl group; n is 0; $Y^4$ is —OCO— or —CO$_2$CH$_2$—; $Y^1$ represents a direct bond, —O—, —CO$_2$— or —OCO—; $Y^2$ represents —CO$_2$—, —OCO—, — a direct bond or —CH$_2$O—; and $Z^1$ and $Z^2$ are each selected from the group consisting of:

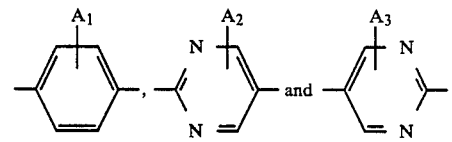

wherein at least two of said $Z^1$ and $Z^3$ groups are the same or different, with the proviso that, not more than one of $Z^1$ and $Z^2$ are a pyrimidine ring at the same time and R is a cyclopropyl group only when $Y^1$ is —CO$_2$; $A^1$, $A^2$ and $A^3$ each represent a fluorine atom, a bromine atom, a chlorine atom, a cyano group or a hydrogen atom and the $\underset{*}{C}$ indicates an asymmetric carbon atom.

2. The optically active cyclopropane compound as set forth in claim 1, wherein $Y^1$ is $-CO_2-$, $Y^2$ is a direct bond, $Z^1$ and $Z^2$ represent a 1,4-phenylene group, and $Y^4$ represents $-CO_2CH_2-$.

3. The optically active cloproprane compound as set forth in claim 1, wherein $Y^1$ represents $-O-$, $Y^2$ is a direct bond, $Z^1$ and $Z^2$ represents a 1,4-phenylene group, and $Y^4$ represents $-OCO-$.

4. The optically active cyclopropane compound as set forth in claim 1, wherein $Y^1$ represents $-OCO-$, $Y^2$ is a direct bond, $Z^1$ and $Z^2$ represent a 1,4-phenylene group, and $Y^4$ represents $-OCO-$.

5. The optically active cyclopropane compound as set forth in claim 1, wherein $Y^1$ represents $-O-$, $Y^2$ is a direct bond, $Z^1$ represents a 1,4-phenylene group, $Z^2$ represents a pyrimidine-2,5-diyl group, and $Y^4$ represents $-OCO-$.

6. The optically active cyclopropane compound as set forth in claim 1, wherein $Y^1$ is a direct bond, $Y^2$ is a direct bond, $Z^1$ represents a pyrimidine-2,5-diyl group, $Z^2$ represents a 1,4-phenylene group, and $Y^4$ represents $-OCO-$.

7. A liquid crystal composition, comprising at least two components, at least one of which is an optically active cyclopropane compound having the formula (I):

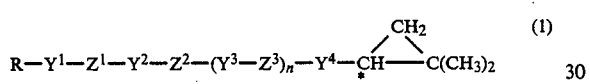

wherein R represents a linear or branched alkyl group of 4-18 carbon atoms or a cyclopropyl group; n is 0, $Y^4$ is $-OCO-$ or $-CO_2CH_2-$; $Y^1$ represents a direct bond, $-O-$, $-CO_2-$ or $-OCO-$; $Y^2$ represents $-CO_2-$, $-OCO-$, O a direct bond or $-CH_2O-$; and $Z^1$ and $Z^2$ are each selected from the group consisting of:

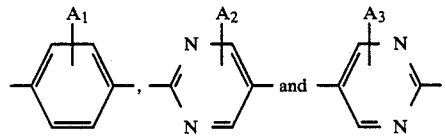

wherein at least two of said $Z^1$ and $Z^2$ groups are the same or different, with the proviso that, not more than one of $Z^1$ and $Z^2$ are a pyrimidine ring at the same time and R is a cyclopropyl group only when $Y^1$ is $-CO_2$; $A^1$, $A^2$ and $A^3$ each represent a fluorine atom, a bromine atom, a chlorine atom, a cyano group or a hydrogen atom and the $$\overset{*}{C}$$

indicates an asymmetric carbon atoms.

8. A liquid crystal composition having a ferroelectric property, which comprises at least two components, at least one of which is an optically active cyclopropane compound having the formula (I):

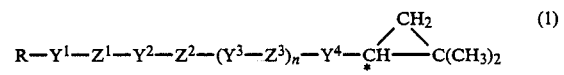

wherein R represents a linear or branched alkyl group of 4-18 carbon atoms or a cyclopropyl group; n is 0, $Y^4$ is $-OCO-$ or $-CO_2H_2-$; $Y^1$ represents a direct bond, $-O-$, $-CO_2-$ or $-OCO-$; $Y^2$ represents $-CO_2-$, $-OCO-$, O, a direct bond or $-CH_2O-$; and $Z^1$ and $Z^2$ are each selected from the group consisting of:

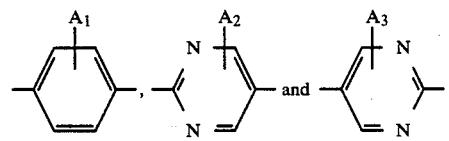

wherein at least two of said $Z^1$ and $Z^2$ groups are the same or different, with the proviso that, not more than one of $Z^1$ and $Z^2$ are a pyrimidine ring at the same time and R is a cyclopropyl group only when $Y^1$ is $-CO_2$; $A^1$, $A^2$, and $A^3$ each represent a fluorine atom, a bromine atom, a chlorine atom, a cyano group or a hydrogen atom and the $$\overset{*}{C}$$

indicates an asymmetric carbon atom, and wherein said liquid crystal composition has a helical pitch of at least 5 μm.

9. The liquid crystal composition as set forth in claim 8, which further comprises at least one smectic C liquid crystalline compound having no optical activity, and which has a helical pitch of at least 5 μm.

* * * * *